(12) United States Patent
Menzel et al.

(10) Patent No.: US 6,174,678 B1
(45) Date of Patent: Jan. 16, 2001

(54) METHODS AND COMPOSITIONS FOR MODULATION OF BACTERIAL TOPOISOMERASE ENZYMES

(75) Inventors: Rolf Menzel, Yardley, PA (US); David A. Elsemore, Lawrenceville, NJ (US)

(73) Assignee: Small Molecule Therapeutics, Inc., Monmouth Junction, NJ (US)

( * ) Notice: Under 35 U.S.C. 154(b), the term of this patent shall be extended for 0 days.

(21) Appl. No.: 09/177,699

(22) Filed: Oct. 23, 1998

Related U.S. Application Data (60) Provisional application No. 60/064,057, filed on Nov. 3, 1997.

(51) Int. Cl.⁷ .............................. C12Q 1/68; C12Q 1/00
(52) U.S. Cl. ........................... 435/6; 435/7.32; 435/7.37; 435/233; 435/18; 435/32; 424/93.2; 536/23.7
(58) Field of Search .................................. 435/233, 6, 18, 435/32, 7.32, 7.37; 536/23.7; 424/93.2

(56) References Cited

U.S. PATENT DOCUMENTS

| | | | |
|---|---|---|---|
| 5,656,495 | 8/1997 | Menzel and Taylor | 435/320.1 |
| 5,910,414 * | 6/1999 | Gwynn et al. | 435/6 |

OTHER PUBLICATIONS

Bjornsti et al., 1989, "Expression of Human DNA Topoisomerase I in Yeast Cells Lacking Yeast DNA Topoisomerase I:Restoration of Sensitivity of the Cells to the Antitumor Drug Camptothecin ", Cancer Res. 49:6318–6323.

Bjornsti and Wang, 1987, "Expression of Yeast DNA Topoisomerase I Can Complement a Conditional—Lethal DNA Topoisomerase I Mutation in *Escherichia coli* ", Proc. Natl. Acad. USA 84:8971–8975.

Chen et al., 1984 "Nonintercalative Antitumor Drugs Interfere with the Breakage–Reunion Reaction of Mammalian DNA Topoisomerase II ", J. Biol. Chem. 259:13560–13566.

DiNardo et al., 1982 "*Escherichia coli* DNA Topoisomerase I Mutants Have Compensatory Mutations in DNA Gyrase Genes", Cell 31:43–51.

Dorman et al., 1989 "DNA Supercoiling in *Escherichia coli*: topA Mutations Can Be Suppressed by DNA Amplifications Involving the tolC Locus ", Molec. Microbiol. 3:531–540.

Drlica and Zhao, 1997, "DNA Gyrase, Topoisomerase IV and the 4–Quinolones", Microbiol. Mol. Biol. Rev.61:377–392.

Drlica and Franco, 1988, "Inhibitors of DNA Topoisomerases", Biochem. 27:2253–2259.

Drolet et al., 1995, "Overexpression of Rnase H Partially Complements the Growth Defect of an *Escherichia coli* ΔtopA Mutant: R–Loop Formation is Major Problem in the Absence of DNA Topoisomerase I ", Proc. Natl. Acad. Sci. USA 92:3526–3530.

Huisman and D'Ari, 1981, "An Inducible DNA Replication–Cell Division Coupling Mechanism in *E. coli*", Nature 290:797–799.

Kenyon et al., 1982, "Regulation of Damage–Inducible Genes in *Escherichia coli* ", J. Mol. Biol. 160:445–457.

Liu, 1990, "Anticancer Drugs that Convert DNA Topoisomerases into DNA Damaging Agents", in: DNA Toplology and Its Biolgical Effects, Cozzarelli and Wang, eds., Cold Spring Harbor Press, pp. 371–389.

Mamber et al., 1990, "Induction of the SOS Response in *Escherichia coli* by Azidothymidine and Dideoxynucleosides", Antimicrobial Agents and Chemother. 34:1237–1243.

Nitiss and Wang, 1988, "DNA Topoisomerase–Targeting Antitumor Drugs Can Be Studied in Yeast", Proc. Natl. Acad. Sci. USA 85:7501–7505.

Peng and Marians, 1993, "*Escherichia coli* Topoisomerase IV", J. Biol. Chem. 268:24481–24490.

Pruss et al., 1986, "Effects of DNA Gyrase Inhibitors in *Escherichia coli* Topoisomerase Mutants ", J. Bacteriol. 168:276–282.

Pruss et al., 1982, "*Escherichia coli* DNA Topisomerase I Mutants: Increased Supercoiling is Corrected by Mutations Near Gyrase Genes", Cell 31:35–42.

Raji et al., 1985, "Genetic Analysis of Mutations That Compensate for Loss of *Escherichia coli* DNA Topoisomerase I", J. Bacteriol. 162:1173–1179.

Reece and Maxwell, 1991, "Probing the Limits of the DNA Breakage–Reunion Domain of the *Escherichia coli* DNA Gyrase A Protein", J. Biol Chem. 266:3540–3546.

Sampson et al., 1989, "Identifications and Characterization of a New Gene of *Escherichia coli* K–12 Involved in Outer Membrane Permeability", Genetics 122:491–501.

Schmid and Sawitzke, 1993, "Multiple Bacterial Topoisomerases: Specialization or Redundancy?", BioEssays 15:445–449.

Taylor and Menzel, 1995, "The Creation of a Camptothecin–Sensitive *Escherichia coli* Based on the Expression of the Human Topoisomerase I", Gene 167:69–74.

(List continued on next page.)

Primary Examiner—Rebecca E. Prouty
Assistant Examiner—Richard Hutson
(74) Attorney, Agent, or Firm—Pennie & Edmonds LLP (57) ABSTRACT

The present invention relates to methods and compositions for the modulation of bacterial topoisomerase enzymes within bacterial cells. More specifically, the present invention relates to bacterial assays wherein the levels of bacterial topoisomerase enzymes or the levels of target sites within the enzymes are varied within bacterial test strains in order to screen for compounds that target, i.e., interact with the topoisomerase enzymes, causing DNA damage and hence, bacterial growth inhibition and/or cell death. The present methods and compositions are useful for the identification and characterization of novel therapeutic antibacterial compounds.

13 Claims, 6 Drawing Sheets

OTHER PUBLICATIONS

Tse–Dinh and Beran–Steed, 1988, "*Escherichia coli* DNA Topoisomerase I is a Zinc Metalloprotein with Three Repetitive Zinc–Binding Domains", J. Biol. Chem. 263:15857–15859.

Vosberg, 1985, "DNA Topoisomerases: Enzymes that Control DNA Conformation", Curr. Top. Microbiol. Immunol. 114:19–102.

Wang, 1994, "DNA Topoismerases as Targets of Therapeutics: An Overview", Adv. Pharmacol., vol. 29A, Liu, ed., Academic Press, pp. 1–19.

Wang, 1987, "Recent Studies of DNA Topoisomerases", Biochem. Biophys. Acta 909:1–9.

Wang, 1985, "DNA Topoisomerases", Annu, Rev. Biochem. 54:665–697.

Flamm et al., 1995, "In vitro evaluation of ABT–719, a noval DNA gyrase inhibitor", Antimicrobial Agents & Chemotherapy 39(4):964–970.

Nakane et al., 1995, "In vitro antibacterial activity DU–6859a, a new fluoroquinolone", Antimicrobial Agents & Chemotherapy 39(12):2822–2826.

* cited by examiner

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggtgaatatg ggtaaagctc                    20

<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2
gctcttccac cagtggc                       17

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgggcagca gccatcatca                    20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttatttctgc gctgcctctt                    20

METHODS AND COMPOSITIONS FOR MODULATION OF BACTERIAL TOPOISOMERASE ENZYMES

This application claims benefit of provisional application No. 60/064,057, filed Nov. 3, 1997.

1. INTRODUCTION

The present invention relates to methods and compositions for the modulation of bacterial topoisomerase enzymes within bacterial cells. More specifically, the present invention relates to bacterial assays wherein the levels of bacterial topoisomerase enzymes or the levels of target sites within the enzymes are varied within bacterial test strains in order to screen for compounds that target, i.e., interact with the topoisomerase enzymes, thereby causing DNA damage and hence, bacterial growth inhibition and/or cell death. The present methods and compositions are useful for the identification and characterization of novel therapeutic antibacterial compounds.

2. BACKGROUND OF THE INVENTION

DNA topoisomerases are enzymes that affect the topology or structure of DNA. More specifically, these enzymes have the ability to introduce supercoils into DNA molecules or relax the DNA molecules; they can catenate or decatenate circular DNA or they can knot or unknot DNA (Schmid et al., 1993, BioEssays 15 (No. 7): 445–449). The DNA topoisomerases act by catalyzing the breakage and rejoining of the DNA phosphodiester backbone (Wang, 1985, Annu. Rev. Biochem. 54: 665–697; Vosberg, 1985, Curr. Top. Microbiol. Immunol. 114: 19–102). These reactions, together with an intervening strand passage event, allow the topoisomerases to alter DNA topology. In fact, correct topoisomerase function is necessary for such basic cellular processes as DNA replication and transcription.

More specifically, the DNA topoisomerases are classified into two types. Type I topoisomerases act by causing a transient break in one strand of the double-stranded DNA and passing one strand of DNA through another, thereby allowing for the relaxation of supercoiled DNA and decatenation of interlocked circular DNA molecules (Schmid et al., supra). In contrast, the Type II DNA topoisomerases alter DNA topology by causing transient breaks in both strands of a double-stranded DNA, allowing the passage of one double-stranded DNA molecule through another. Like the Type I DNA topoisomerases, the Type II topoisomerases also allow the relaxation and decatenation of DNA; however, one bacterial Type II topoisomerase, DNA gyrase, also has the ability to introduce negative supercoils into relaxed DNA. In either type of topoisomerase, after the strand passage event, the final step of the reaction is the rejoining or ligation of the DNA break(s).

Analysis of the mechanism of action of the DNA topoisomerases on the molecular level indicates that these enzymes introduce breaks in the DNA molecule by forming a covalent phosphotyrosine bond between a specific tyrosine amino acid residue present on the topoisomerase and the phosphodiester backbone of the DNA. Thus, an intermediate in the catalytic reaction of these enzymes is a covalently-linked enzyme-DNA complex, sometimes termed the cleavable complex (see, e.g., Liu, 1990, DNA Topology and Its Biological Effects, Cozzarelli and Wang (eds.), Chapter 14, pp. 371–372, Cold Spring Harbor Press). It is this cleavable complex that forms the molecular target for therapeutic compounds that can interact with this intermediate, stabilizing it, i.e., trapping it, such that the subsequent DNA strand ligation step of the reaction cannot be completed.

In bacteria, two Type I topoisomerase enzymes have been described: Topoisomerase I (Topo I) and Topoisomerase III (Topo III). Topo I, encoded by the topA gene, is responsible for the major DNA relaxing activity of the cell, and catalyzes the relaxation of DNA through the sequential breakage-strand-passage-religation cycle common to all topoisomerase enzymes. Topo III represents a minor activity encoded by the topB gene, is less well-characterized and its role in vivo is less clear, although the molecule appears to possess decatenation activity (Scmid et al., supra at p. 447). Bacteria also have two Type II topoisomerases: DNA gyrase (Topo II) and Topoisomerase IV (Topo IV). As noted supra, DNA gyrase catalyzes negative supercoiling in DNA; Topo IV has been found to catalyze decatenation of interlinked DNA, e.g., subsequent to DNA replication, as well play a role in DNA relaxation. Although Topo IV shares extensive homology with DNA gyrase (40–50% amino acid identity), it differs from DNA gyrase in the activities it can catalyze. For example, Topo IV cannot couple the hydrolysis of ATP to the process of DNA supercoiling as gyrase can, but it is able to relax DNA in an ATP-stimulated fashion.

In contrast to the bacteria, eukaryotes, such as yeast and humans, possess a single Type I DNA topoisomerase (see, e.g., Wang, J. C., 1987, J. Biochem. Biophys. Acta. 909: 1–9). Furthermore, this eukaryotic topoisomerase is distinct from bacterial Topo I in both structure and function. For example, the bacterial and eukaryotic Topo I enzymes share no amino acid sequence homology. In addition, the eukaryotic enzyme shows a preference for binding double-stranded DNA and catalyzes its reaction by forming a covalent 3'-phosphodiester intermediate. In contrast, the bacterial Topo I enzyme shows a preference for binding at the junction of double and single-stranded regions and catalyzes its reaction by forming a 5'-phosphodiester intermediate (see, e.g., Taylor and Menzel, 1995, Gene 167: 69–74). Finally, it is of interest to note that, while the human Topo I enzyme is the target of the antitumor drug camptothecin (CPT), the bacterial enzyme is resistant to that drug. Eukaryotes also possess a Type II DNA topoisomerase that demonstrates some structural and evolutionary relationship to bacterial gyrase (Wang, 1994, Advances in Pharmacology, Volume 29A, Liu (ed.), Academic Press).

While the bacterial Type I topoisomerase, Topo III, appears to be non-essential to the viability of the cell (Hiasa, et al., 1994, J. Biol. Chem. 269: 2093–2099), Topo I is essential in an otherwise normal bacterial cell. Nevertheless, the topA gene may be deleted or otherwise rendered inactive, provided that certain second site compensatory mutations are present in the topA$^-$ strains, leading some to question the essential nature of the bacterial Topo I enzyme (Pruss et al., 1982, Cell 31: 35–42; DiNardo et al., 1982, Cell 31: 43–51).

Second site mutations that compensate for the loss of topA do so by altering the activity or levels of other topoisomerase enzymes in the mutant host cell. For example, mutations that compensate for the loss of bacterial Topo I have been mapped to the two genes (gyrA and gyrB) that encode the bacterial Type II DNA topoisomerase, DNA gyrase. These mutations have been shown to reduce the levels and activity of DNA gyrase, suggesting a balance between the competing activities of topoisomerases that introduce DNA supercoils (i.e., DNA gyrase) and those that remove or relax DNA supercoils (e.g., Topo I).

Still other mutations that compensate for the loss of topA in a topA mutant have been mapped to a region of the chromosome encoding the parC and parE genes which encode the subunits of the bacterial Type II topoisomerase, Topo IV. The majority of these compensatory mutations are duplications of the parC,E region of the chromosome. Such duplications are believed to increase the copy number, and hence the level, of Topo IV within the bacterial cell. It has also been shown that extra copies of Topo IV-encoding sequences on a plasmid are able to compensate for a loss of topA.

As noted supra, compounds that can trap the cleavable complex intermediate formed during the catalytic reaction of the DNA topoisomerases represent important drugs. For example, compounds that trap the covalent intermediates involved in the catalytic reactions of the eukaryotic DNA topoisomerases have been shown to represent important anticancer drugs; e.g., the anticancer drugs Etoposide and Adriamycin trap the covalent intermediate of human Type II topoisomerases. As noted supra, camptothecins, another important class of anticancer drug, trap the DNA intermediate of human Type I topoisomerase but do not affect the bacterial Type I topoisomerases (Drlica, K. et al., Biochem. 27: 2253–2259). In the area of antibacterial drugs, a major class of antibiotics, the quinolones, have been shown to trap the cleavable complex of the bacterial DNA gyrase enzyme. The quinolones have also been shown to trap the intermediate formed during the catalytic reaction of Topo IV (Drlica et al., September 1997, Microbiology and Molecular Biology Reviews, 61 (No. 3): 377–392).

Model systems for the study of eukaryotic Type I DNA topoisomerases have been reported (Nitiss, J. et al., 1988, Proc. Natl. Acad. Sci. USA 85: 7501–7505; M. -A., Bjornsti et al., 1989, Cancer Research 49: 6318–6323; Menzel, R. et al., U.S. Pat. No. 5,656,495). To date, however, no model systems exist for the systematic identification of compounds which target the bacterial DNA topoisomerases. Furthermore, no bacterial assays have been reported which utilize varying levels of bacterial DNA topoisomerase targets within bacterial cells to screen for drugs that interact with those enzymes in the identification of antibacterial compounds, as disclosed herein. The methods and compositions of this invention can lead to the identification and use of important new antibacterial compounds.

3. SUMMARY OF THE INVENTION

The present invention relates to methods and compositions for the identification of new antibacterial compounds. More specifically, the present invention relates to bacterial assays or screens, wherein the levels of bacterial DNA topoisomerases or target sites within the topoisomerases are varied in bacterial test strains in order to identify compounds that target, i.e., interact with topoisomerase enzymes within the bacterial cell, thereby causing DNA damage which leads to cell growth inhibition and/or cell death. The methods and compositions of the invention therefore identify potent antibacterial compounds that act through their effects on bacterial DNA topoisomerases.

According to this invention, screens are performed for identifying test compounds that arrest the reaction catalyzed by the bacterial DNA topoisomerases. Such compounds are referred to as "poisons" and, as herein defined, these poisons interact with the DNA topoisomerase cleavable complex intermediate, trapping the intermediate and thus blocking the DNA rejoining step of the topoisomerase catalytic reaction. As such, these poisons possess an antibacterial therapeutic effect, not through inhibition of the catalytic activity of the enzyme per se, but rather via their ability to cause lethal DNA damage (see, e.g., Liu, supra at pp. 371–372; Wang, supra at p. 9). For example, one class of poisons acts to trap the bacterial Topo I cleavage complex intermediate. Another class of poisons acts to trap the bacterial Type II DNA topoisomerases, e.g., DNA gyrase and Topo IV.

The assays or screens of this invention comprise contacting a test compound to a bacterial test strain A and a bacterial test strain B wherein the test strains are isogenic, except that the two strains exhibit a differential level of test compound topoisomerase "targets", that is, elements or sites within the topoisomerase enzyme that allow interaction with the test compound or poison. According to this invention, a differential level of such targets can be achieved by decreasing or increasing the level of the topoisomerase enzyme itself (e.g., via deletion or duplication mutations) or by decreasing or increasing the number of functional sites within the enzyme that allow interaction with the test compound or poison.

Since it is the presence of the topoisomerase target that enables a topoisomerase poison to exert its antibacterial effect, i.e., DNA damage (due to the interaction between the poison and the target intermediate), elevated levels of the topoisomerase target in one test strain relative to another leads to a differential, e.g., increased sensitivity to the test compound that can be measured as a function of DNA damage. Therefore, if, upon exposure of test strains A and B as defined above to a test compound, a differential sensitivity is detected between the two strains, that test compound is identified as a DNA topoisomerase poison. As used herein, "differential sensitivity" refers to a differential amount or measure of DNA damage to the bacterial cells, which can be detected by assays of cell death and/or growth inhibition of the cells (indirect measures of DNA damage) or by standard DNA damage or DNA cleavage assays (direct measures). According to a preferred embodiment, a differential sensitivity between the test strains is first detected using an indirect measure of DNA damage such as a growth inhibition assay and the DNA damage ability/activity of the test compound/poison is further confirmed by standard DNA damage or cleavage assays using known substrates (see, e.g., Sections 6.4 and 6.5, infra).

The assays and compositions of this invention are useful for the identification of either bacterial Topo I poisons or bacterial Type II topoisomerase poisons. Thus, according to one embodiment of the present invention, a screen for identifying Topo I poisons comprises contacting a test compound to two bacterial test strains that are isogenic except that one of the strains has a reduced level of Topo I enzyme targets relative to the other. The differential inhibition of growth and/or cell death exhibited by the two strains relative to each other is measured. Alternatively or additionally, assays and biochemical tests can be performed to determine the differential DNA damage exhibited by the two test strains. A test compound that causes an increased amount of DNA damage, growth inhibition and/or killing of the strain that has the elevated level of Topo I targets relative to the other strain indicates that the test compound works in concert with Topo I to poison the cell; that test compound is therefore identified as an antibacterial Topo I poison.

According to one embodiment of this invention, bacterial test strains A and B are isogenic strains that differ only in that one strain contains a topA mutation which decreases the level of Topo I or Topo I targets within the bacterial cell. According to a preferred embodiment, the topA mutation is a deletion mutation. A test compound is contacted to the test strains and the differential sensitivity of the strains relative to each other is measured. A test compound that demonstrates a differential, in this case, an increased DNA damage, growth inhibition and/or killing of the wild type bacterial strain relative to the topA mutant strain is identified as a Topo I poison.

In another embodiment, a single bacterial test strain containing a topA mutation that results in a loss or decreased level of Topo I targets additionally contains a second DNA sequence encoding a functional topA gene. For example, the strain can contain a plasmid or other extrachromosomal DNA sequence having a functional topA gene under the regulatory control of an inducible promoter for the regulated production of Topo I. Alternatively, a functional topA gene operably linked to an inducible promoter may be inserted directly into the bacterial DNA. According to this embodiment, the strain is studied under two different conditions: in one, the strain is induced to express Topo I, while in the other, it is not. As with the Topo I poison screen discussed supra, a test compound that causes a differential DNA damage, growth inhibition and/or killing of the bacterial strain induced to produce Topo I relative to the non-induced topA mutant strain is identified as a Topo I poison. According to a preferred embodiment, the topA mutation is a deletion mutation.

According to another embodiment of the present invention, a screen for identifying bacterial Type II DNA topoisomerase poisons comprises contacting a test compound to two bacterial test strains that are isogenic except for the fact that one of the strains has a reduced level of bacterial Type II DNA gyrase targets and the second strain has an increased level of Type II Topo IV targets. According to a preferred embodiment, the levels of the enzymes themselves are varied such that one of the strains has a reduced level of the bacterial gyrase enzyme and the other strain has an increased level of the Topo IV enzyme. The strain with reduced levels of the gyrase enzyme will possess a decreased number of targets for a Type II-specific poison whereas the strain with increased levels of Topo IV will possess an increased level of targets for a Type II-specific poison. A differential, in this case, increased DNA damage, growth inhibition and/or cell death exhibited by the strain with the elevated level of Type II DNA topoisomerase relative to the strain having reduced levels of Type II targets indicates that the test compound works in concert with the Type II topoisomerase enzymes to poison the cell. Such a test compound is identified according to the assays of this invention as an antibacterial Type II DNA topoisomerase poison.

According to one embodiment of this invention, the isogenic test strains are topA$^+$ and according to another embodiment, they are topA$^-$. In an alternative embodiment, a bacterial strain with reduced gyrase levels and a bacterial strain with increased Topo IV levels are compared respectively, i.e., separately, to isogenic strains that are wild type for each mutation in order to identify Type II poisons that are specific for the gyrase or Topo IV enzymes.

As noted supra, in topA mutants, the topA mutations must be compensated for by second site mutations in order for the bacterial cells to maintain their viability. All topA$^-$ strains used in the embodiments of this invention therefore further comprise mutations which compensate for topA defects, including but not limited to mutations in the gyrA and/or gyrB genes or in the parC and/or parE genes.

5. DETAILED DESCRIPTION OF THE INVENTION

The present invention relates to bacterial assays or screens that allow the identification of compounds or "poisons" that possess antibacterial activity through their effects on the bacterial DNA topoisomerases.

The term "poison" as used herein refers to compounds that interact with the cleavable complex intermediate formed during the catalytic reaction of the bacterial DNA topoisomerases. Such poisons trap the intermediate and block the DNA rejoining step of the catalytic reaction. These types of compounds thus exert their antibacterial effect by damaging the DNA of the bacterial cell (see, e.g., Liu, supra at pp. 371–372; Wang, supra at p. 9). As used herein, the term "Topo I poison" refers to those compounds that act by trapping the cleavable complex intermediate of bacterial Type I Topoisomerase I, also referred to herein as Topo I. The term "Type II poison" refers to those compounds that act by trapping the cleavable complex intermediate of bacterial Type II topoisomerases, such as DNA gyrase or Topo IV.

In order to identify and isolate the antibacterial DNA topoisomerase poisons described above, the present invention provides bacterial assays wherein the levels of bacterial DNA topoisomerase enzyme targets are varied in bacterial test strains, thus providing differential levels of targets for topoisomerase poisons. According to this invention, the bacterial test strains are isogenic, except that the strains possess differential levels of DNA topoisomerase targets. According to a preferred embodiment, the strains possess differential levels of DNA topoisomerase enzymes. The test strains are then exposed to a test compound and the differential sensitivity of the strains to the compound is assessed. As noted supra, a differential sensitivity exhibited by the bacterial cells according to this invention is a differential amount or degree of DNA damage, which can be detected by cell death or growth inhibition assays such as growth sensitivity assays which can be performed in liquid culture media employing microtiter plates or growth sensitivity assays in agar such as that described in Section 6.2 infra, wherein differential sensitivity to the test compound is measured by assessing zones of growth inhibition.

Alternatively, the DNA damage inflicted on the bacterial cells by these poisons may be identified by direct DNA damage or DNA cleavage assays or techniques known in the art. For example, an alkali elution profile of cleaved DNA is a well-known method for demonstrating DNA damage (see, e.g., Markovitz et al., 1987, Cancer Research 47: 2050–2055). Alternatively, a DNA damage inducible promoter assay can be used, wherein the level of DNA damage is assessed by measuring the level of a reporter gene whose expression is driven by a regulatory sequence induced by the DNA damage. Such DNA damage-inducible regulatory sequences can be introduced into the test strains prior to the screen and include, but are not limited to, promoters induced as part of the bacterial SOS response. For example, one such regulatory sequence is the sulA promoter sequence, the sequence of which is well known to those of skill in the art (see, e.g., Mamber et al., 1990, Antimicrobial Agents and Chemotherapy 34: 1237–1243 and Kenyon et al., 1982, J. Mol. Biol. 160: 445–457). Thus, the DNA damage caused by a potential topoisomerase poison can be detected, for example, by measuring the level of a reporter gene product whose expression is driven by the sulA promoter sequence.

The reporter sequence can be any detectable gene product. Reporter sequences can include, but are not limited to, LacZ (betagalactosidase) and CAT (chloramphenicol acetyltransferase) gene products. Methods for detection using reporter sequences including, but not limited to those described above, are well known to those of skill in the art. An $E.coli$ strain, referred to herein for exemplary purposes only, which contains a sulA-lac construct as a DNA inducible reporter construct is $E.coli$ strain GR4413 (Huisman, O. et al., 1981, Nature 290:797–799). See, e.g., Taylor and Menzel, 1995, Gene 167: 69–74 for an example of the use of a sulA-lac regulatory-reporter construct in a DNA damage assay.

According to a preferred embodiment of the invention, the differential DNA damage exhibited by the test strains due to a test compound is detected using a growth inhibition assay, preferably in agar (see Section 6.2, infra). This allows for a more rapid and efficient screening of many compounds in as short a time as possible. The DNA damage activity of a test compound identified as a poison according to this screen can then be further confirmed by various DNA damage or cleavage assays as exemplified infra in Sections 6.4 and 6.5. More specifically, the DNA damage assay of Section 6.4 can be used to demonstrate actual DNA cleavage that is dependent on the presence of both the specific purified DNA topoisomerase enzyme and the poison compound in question (see, e.g., Anderson et al., 1994, in Topoisomerase Biochemistry and Molecular Biology, Liu (ed.), pp. 83–101).

Since, according to this invention, the topoisomerase poison requires the presence of the topoisomerase target for its antibacterial effect, elevated levels of the target in one test strain relative to another leads to a differential, and in such a case, increased sensitivity to a test compound that acts as a topoisomerase poison. Conversely, reduced levels of the topoisomerase target in one test strain, e.g., in a topA deletion mutant relative to an otherwise isogenic wild type strain, leads to a differential sensitivity and in that case, a decreased sensitivity on the part of the mutant strain to a test compound that is a topoisomerase poison.

It is of interest to note that the drug screening approach of this invention is therefore unlike the more traditional drug screening approaches, where the desired cytotoxic effect of a drug is due to a simple inhibition of a target gene product and therefore reduced target levels result in a greater sensitivity to the drug. As indicated, in the present invention, the drug or antibacterial compound requires the target gene product in order to have its cytotoxic effect and therefore reduced target levels result in a greater resistance to the antibacterial compound, while elevated target levels result in a greater sensitivity to the drug.

Test compounds that can be screened for antibacterial activity using the methods and compositions of this invention include, but are not limited to, compounds obtained from any commercial source, including Aldrich (1001 West St. Paul I-Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, L.A. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the methods of the invention, including microbial, fungal or plant extracts.

Furthermore, diversity libraries of test compounds, including small molecule test compounds, may be commercially obtained from Specs and BioSpecs B.V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), and Asinex (Moscow, Russia). Combinatorial libraries of test compounds, including small molecule test compounds, can be may be generated as disclosed in Eichler & Houghten, 1995, Mol. Med. Today 1:174–180; Dolle, 1997, Mol. Divers. 2:223–236; Lam, 1997, Anticancer Drug Des. 12:145–167. These references are incorporated hereby by reference in their entirety.

The present invention is divided into the following sections solely for the purpose of description: (a) methods and compositions for screening for bacterial Topo I poisons; and (b) methods and compositions for screening for bacterial Type II topoisomerase poisons. It is to be noted that for each of the methods described below, according to one embodiment of the invention, the bacterial test cells utilized are those that are particularly permeable, thereby facilitating entry of the test compounds into the cells. For example, such cells can include, but are not limited to, cells with imp mutations. Among the imp mutations that can be utilized in this regard is the imp 4213 mutation (Sampson, B. A. et al., 1989, Genetics 122:491–501). Furthermore, bacterial strains that can be used in the screens of this invention include, but are not limited to, $E.$ $coli,$ $Salmonella$ $typhimurium,$ $S.$ $aureus,$ $S.$ $fecalis,$ $P.$ $aeruginosa,$ $M.$ $tuberculosis,$ and $H.$ $pylori.$

5.1. Methods and Compositions for Screening for Bacterial Topo I Poisons

According to the present invention, bacterial screens are provided for identifying bacterial Topo I topoisomerase poisons. These bacterial assays comprise contacting a test compound to two bacterial test strains that are isogenic except that one of the strains has a reduced level of bacterial Topo I enzyme targets relative to the other. After an appropriate exposure to the test compound, the differential sensitivity of the test strains to the test compound is determined. A test compound that causes an increased amount of DNA damage, growth inhibition and/or killing of the strain that has the elevated level of Topo I targets relative to the other strain is identified as an antibacterial Topo I poison.

According to one embodiment of this invention, isogenic bacterial test strains A and B differ only in that one strain is topA⁻. As used herein, the term "topA⁻" refers to any topA mutation that decreases the level of Topo I or Topo I targets within the cell, including but not limited to a deletion of the topA gene. According to a further preferred embodiment of this invention, isogenic bacterial test strains A and B differ only in that one strain contains a topA deletion mutation or other genetic alteration of the topA gene and thereby exhibits greatly reduced levels of the bacterial Topo I enzyme or is missing the enzyme entirely. See FIG. 2 for an illustration of the genetic events involved in the construction of a bacterial strain containing a topA deletion. As noted supra, in order to retain their viability for these screens, topA mutant strains must possess a second site mutation, such as in the gyrA and/or gyrB genes, or in the parC and/or parE genes, in which the second site mutation compensates for the loss of the relaxing activity of the Topo I enzyme. In the case of mutations in the gyrA or gyrB genes, such mutations reduce the endogenous supercoiling activity of the gyrase enzyme and thus compensate for the loss of the relaxing activity normally provided by the Topo I enzyme. In the case where the second site mutation involves duplications in the parC and/or parE genes, such mutations provide increased relaxing activities to the cell, thus compensating for the relaxing activity lost via the topA mutation (see FIG. 1).

Since the strains used in this embodiment of the invention must be isogenic except for the absence or presence of the topA mutation, the non-topA⁻ test strain must also contain the same compensatory second site mutations contained in the topA mutant strain. Strains that can be used according to this invention include *E.coli* RFM475(gyrB$^{ts}$ topA⁻) (Drolet, 1995, Proc. Natl. Acad. Sci. 92: 3526–3530) and its companion strain RFM445 (gyrB$^{ts}$ topA⁺) (Taylor and Menzel, 1995, Gene 167: 69–74) or GP203 (gyrA(Nal$^r$) topA⁻) and its companion strain GP202 (gyrA(Nal$^r$) topA⁺) ((Pruss et al., 1986, J. Bacteriol. 168 (No. 1): 276–282).

Figure 1A:
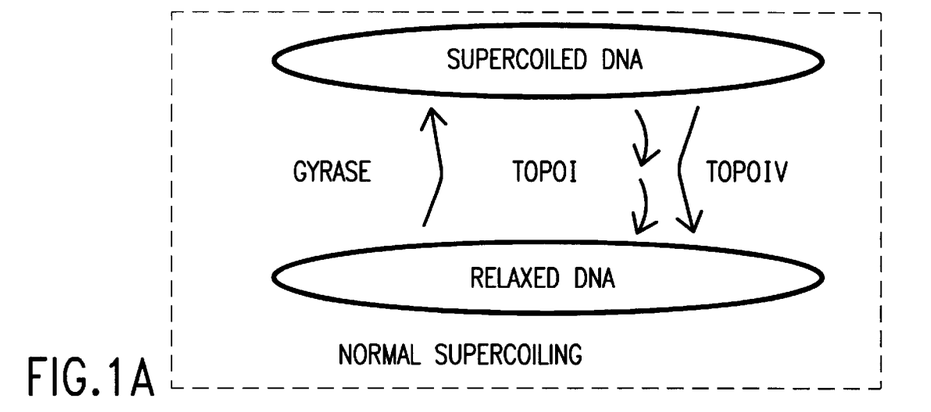
FIGS. 1A–1C. FIG. A) A schematic diagram showing that various bacterial DNA topoisomerases act in concert to maintain a balance in the level of DNA supercoiling. FIG. B) Reducing DNA gyrase activity, and thereby restoring the balance by decreasing DNA supercoiling activity, can compensate for the loss of topA. FIG. C) Increasing Topo IV activity, and thereby restoring the balance by increasing DNA relaxing activity, will also act to compensate for the loss of topA.
Figure 1B:
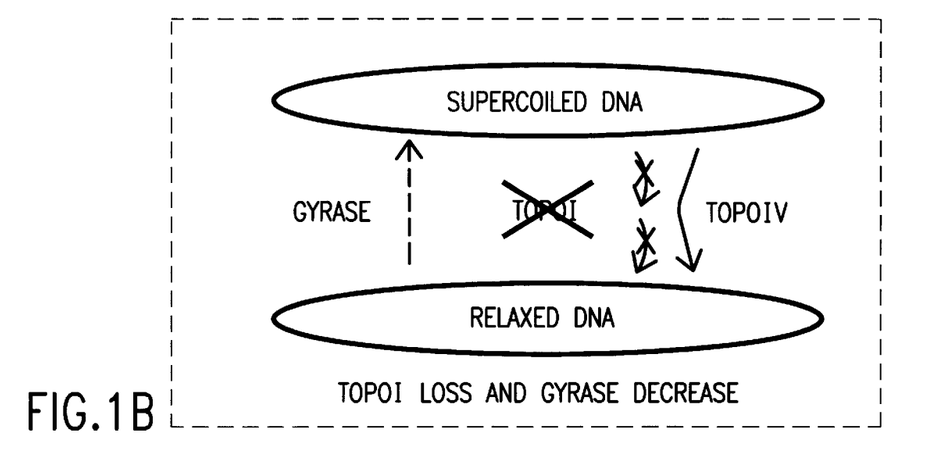
Figure 1C:
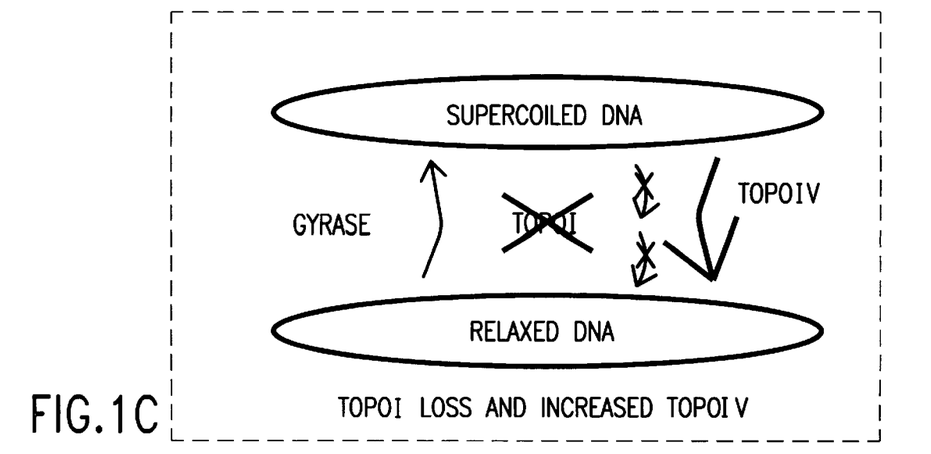
Figure 2:
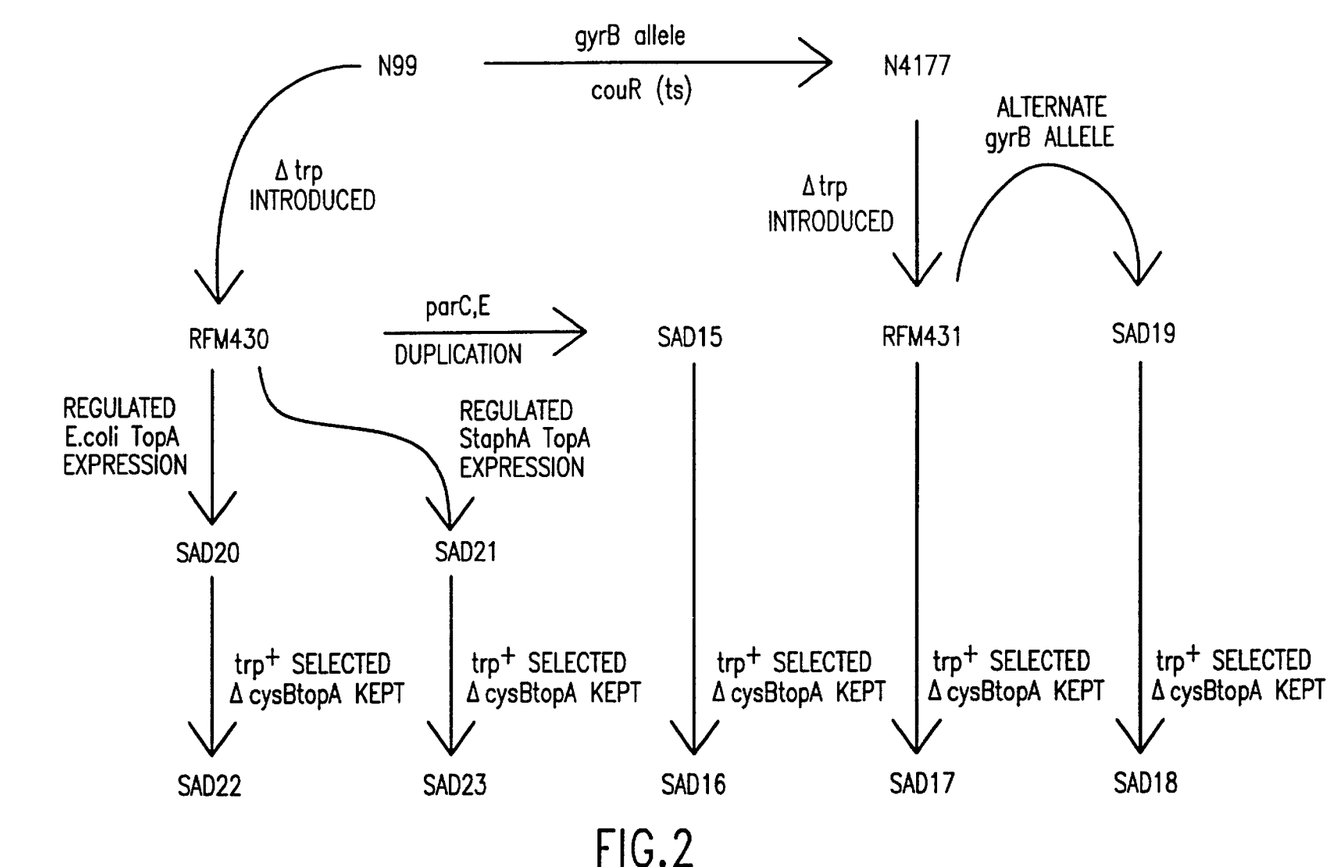
FIG. 2. Series of genetic events involved in the construction of isogenic strains for the identification of bacterial Topo I and Type II topoisomerase poisons.

Although such existing strains may be used according to this invention, a carefully constructed set of isogenic strains involving a minimum set of genetic manipulations is desired so as to reduce strain differences to only those genes under consideration. Novel sets of isogenic strains can be constructed in accordance with this invention as described in Section 6.1 and Table I, infra and as depicted in FIG. 2. Novel strains for use in the Topo I screen of this invention include topA-wild type strain SAD15 and its isogenic topA-deleted companion strain SAD16; topA-wild type strain RFM431 and its isogenic topA-deleted companion strain SAD17; and topA-wild type strain SAD19 and its isogenic topA-deleted companion strain SAD18 (see FIG. 4A and Table I, infra). See also, Table II, in Section 6.2 infra, which lists pairs of isogenic test strains that can be used in the Topo I and Type II poison screens of this invention.

According to this embodiment of the invention, a test compound is contacted to the test strains and the differential sensitivity of the strains relative to each other is measured. A test compound that acts by trapping the cleavable complex intermediate of the Topo I enzyme will only inhibit or kill a strain that possesses the target enzyme, but will have no effect on a strain that is lacking Topo I. Thus, a test compound that demonstrates a differential (i.e., increased) DNA damage, growth inhibition and/or killing of the wild type bacterial strain relative to the topA mutant strain is identified as a Topo I poison. See FIG. 4A for a depiction of this screening embodiment of the invention.

Figure 3A:
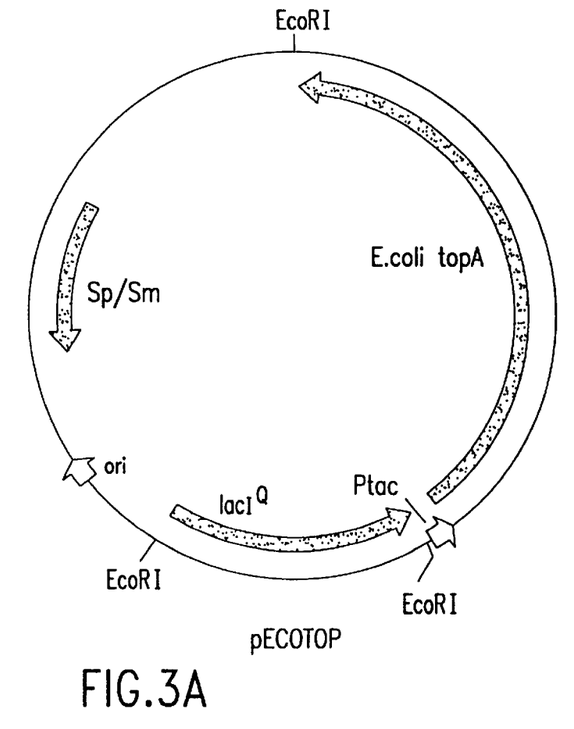
FIGS. 3A–3B. Schematic diagrams of the plasmids used for the inducible expression of E. coli topoisomerase I (FIG. 3A) and S. aureus topoisomerase I (FIG. 3B).
Figure 3B:
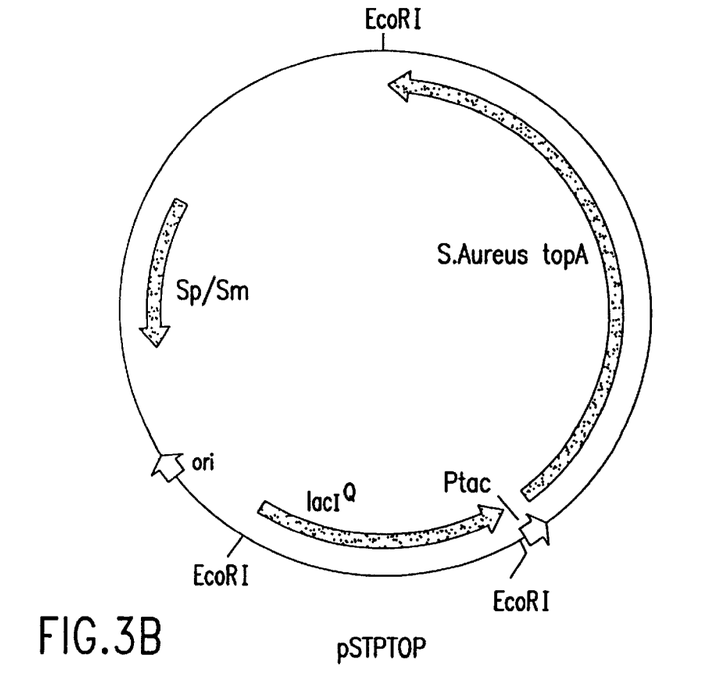

In another embodiment of the invention, a single bacterial test strain contains a topA deletion and therefore lacks the Topo I target enzyme, but it additionally contains a second DNA sequence encoding a functional topA gene under the regulatory control of an inducible promoter for the regulated production of Topo I. For example, the strain can contain a second DNA sequence inserted into its bacterial DNA or it can contain a plasmid or other extrachromosomal DNA sequence that carries a functional bacterial topA gene operably linked to an inducible promoter. Examples of inducible promoters that can be used for the regulated expression of Topo I according to this invention include the tac promoter, the lac promoter and ara- and tet-based systems (see, e.g., Lutz and Bujard, March 1997, Nucl. Acids. Res. 25: 1203–1210). FIGS. 3A and 3B represent schematic depictions of plasmids that can be used according to this embodiment of the invention for the inducible expression of bacterial Topo I. The recombinant techniques for producing the plasmids utilized according to this embodiment of the invention are well known to those of skill in the art. See, e.g., Sambrook et al., 1989, Molecular Cloning, A Laboratory Manual, Cold Spring Harbor Press, NY; and Ausubel et al., 1989–1997, Current Protocols in Molecular Biology, Green Publishing Associates and Wiley Interscience, NY, both of which are incorporated herein by reference in their entirety. For details of the construction of the pECOTOP and pSTP-TOP plasmids depicted in FIGS. 3A and 3B, see Section 6.1, infra. Novel test strains containing inducible topA genes that can be used according to this embodiment of the invention include SAD22 and SAD23, which strains can be constructed as described infra in Section 6.1.

Figure 4A:
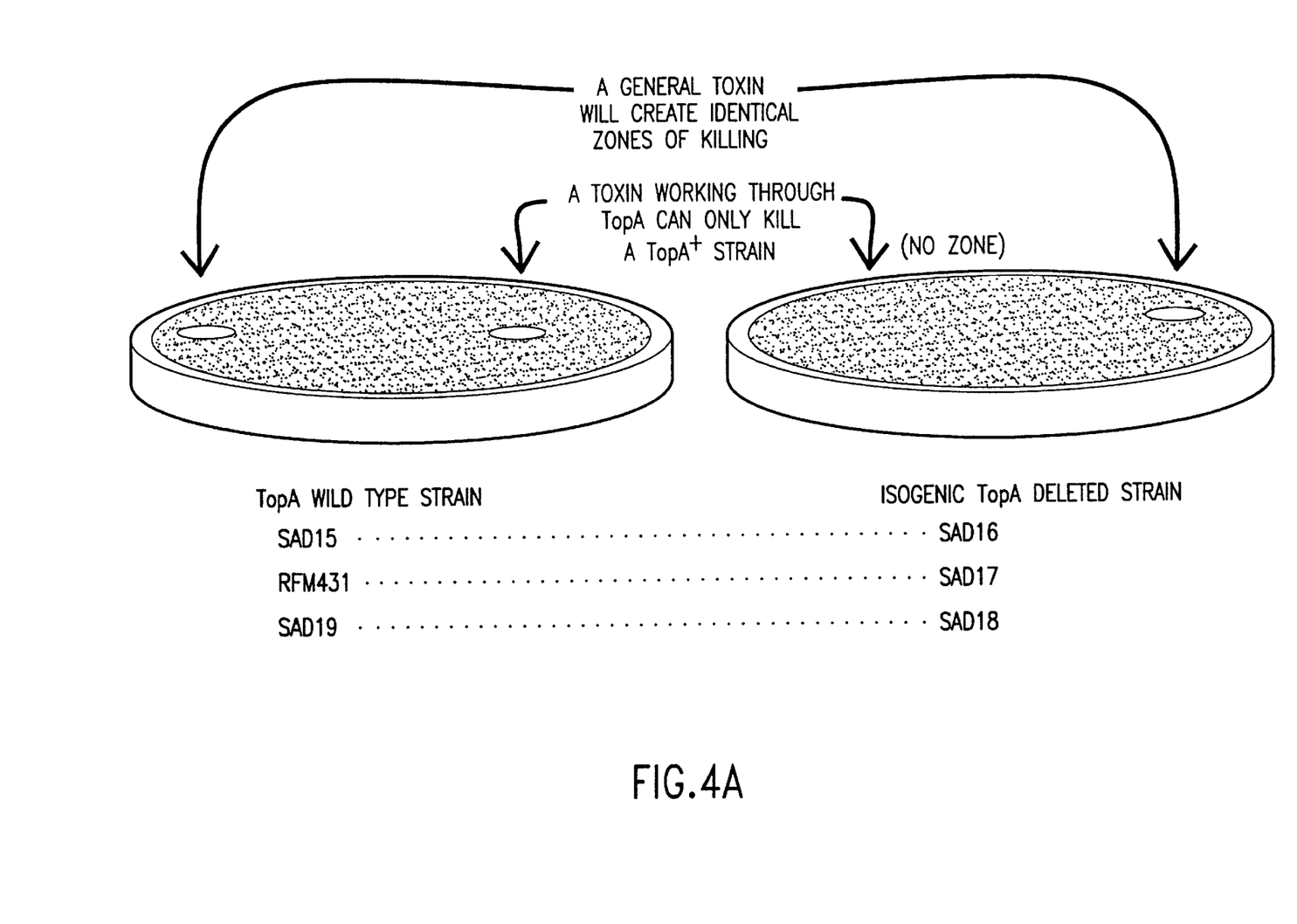
FIGS. 4A and 4B. Schematic depiction of a Topo I topA deletion screen (FIG. 4A) and a Topo I inducible expression screen (FIG. 4B).
Figure 4B:
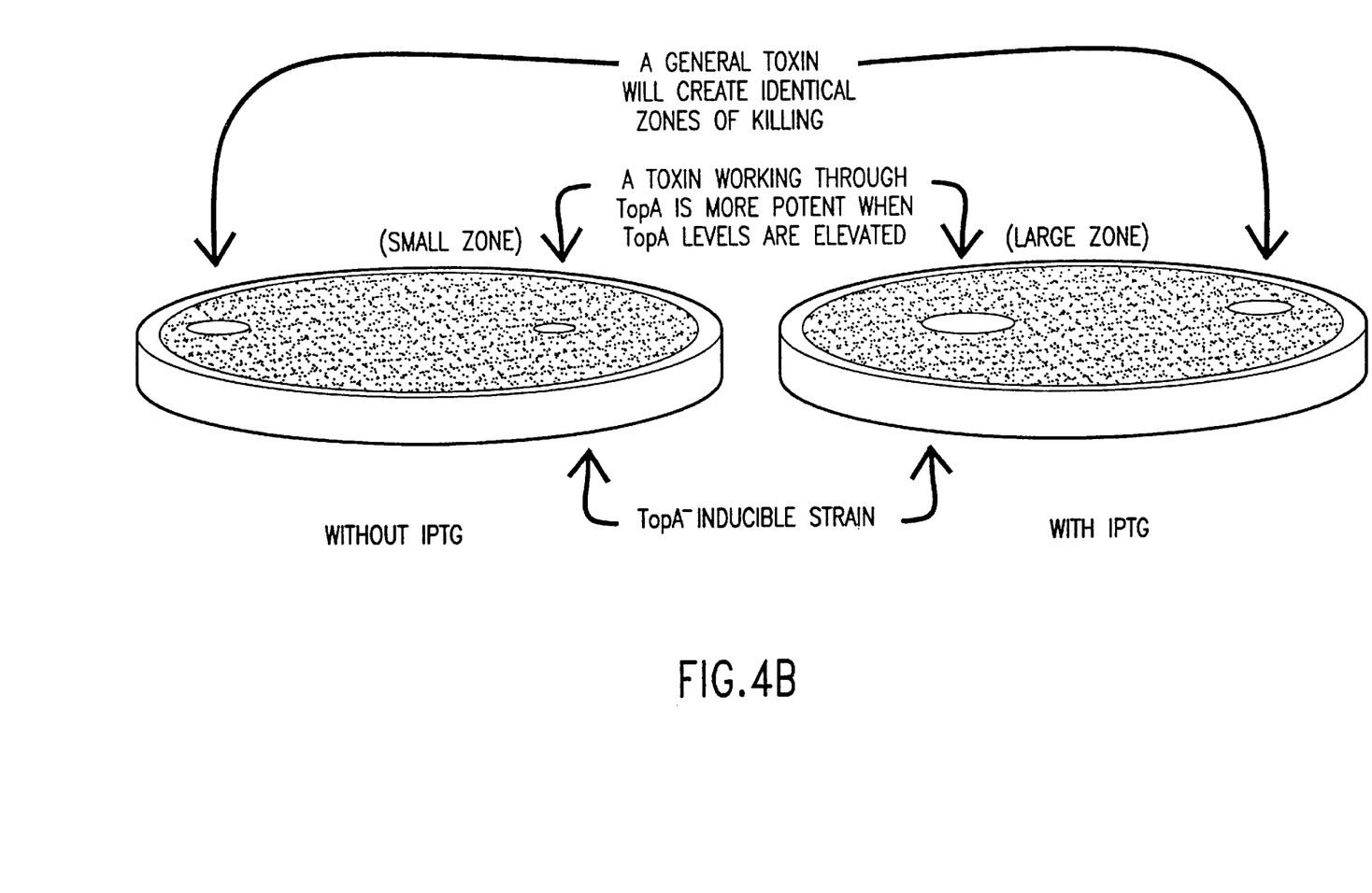

Thus, according to this embodiment, the bacterial strain is studied under two different conditions; it is either induced to express Topo I or it is not (see FIG. 4B). The regulated expression of the topA gene according to this embodiment provides the ability, in a single strain, to examine conditions of no or low expression versus conditions of high level expression. Since the general viability of topA⁻ strains (without compensatory mutations) is weak, it is preferred to carry out this screen using low versus high induction conditions. In a preferred embodiment of the invention, basal (non-induced) Topo I levels are less than 10% of wild type levels (as assayed by Western analysis) and induction produces a greater than 5-fold increase over basal levels (as assayed by Western analysis). Higher level expression of the topA gene results in an increased sensitivity to a Topo I poison since the poison converts the target into a toxic agent. Thus, as with the Topo I poison screen discussed supra, a test compound that causes an increased sensitivity, i.e., DNA damage, growth inhibition and/or killing of the bacterial strain, when induced to produce Topo I relative to the non- or low-induced condition is identified as a Topo I poison.

Additionally, this embodiment of the invention provides a drug screening assay that can be set up to evaluate levels of Topo I expression in excess of those that would be tolerated under normal conditions. According to one embodiment, a topA-deleted test strain containing a plasmid bearing the topA gene can be induced to produce higher than normal levels of Topo I. That strain can then be compared with an otherwise isogenic strain that is wild type for topA and the differential sensitivity to test compounds determined. Alternatively, isogenic topA⁺ strains with inducible topA genes such as SAD20 or SAD21 (which can be constructed as described infra in Section 6.1) can be used to compare induced versus uninduced conditions. For example, SAD20 could be induced to produce higher than normal levels of Topo I and compared to an SAD20 culture that is uninduced and produces wild-type levels of Topo I.

According to another embodiment of the invention, *E.coli* can be used as the host for the expression of topA gene products from other bacteria such as *S. aureus* (see FIG. 3B and Section 6.1, infra). The topA gene from other pathogens such as *Salmonella typhimurium, S. fecalis, P. aeruainosa, M. tuberculosis,* and *H. pylori* could also be used. The use of a pathogen-specific target, e.g., Topo I of *S. aureus,* in the screens of this invention may be desirable in cases where pathogen-specific antibacterial agents are sought.

In any of the screens of this invention as described above, it is preferable to confirm that the Topo I poison identified by the screen causes DNA damage within the bacterial cell. As noted supra and as exemplified infra in Section 6.4 and 6.5, such confirmation can be achieved using techniques known in the art such as DNA damage assays and/or DNA cleavage assays.

5.2. Methods and Compositions for Screening for Bacterial Type II Poisons

As noted supra, in topA$^-$ bacterial strains, the loss of topA function can be compensated for in different ways. A reduction in the level of the bacterial Type II topoisomerase enzyme, DNA gyrase, which aids in supercoiling of the DNA, can compensate for the loss of the DNA relaxing activity of Topo I, while, alternatively, an increase in the levels of Topo IV, which possesses its own DNA relaxing activity, can compensate for the loss of the Topo I relaxing activity.

These two distinct mechanisms of compensating for the loss of Topo I have very different consequences with respect to the number of Type II topoisomerase targets in the bacterial cell. TopA$^-$ strains that compensate for the topA defect via reduced gyrase levels will have reduced levels of Type II topoisomerase targets (reduced gyrase plus normal Topo IV), while topA-deleted strains that compensate for the topA defect via increased Topo IV levels will have increased Type II topoisomerase targets (normal gyrase plus elevated Topo IV). The cells with increased levels of Type II topoisomerase targets will therefore display an increased sensitivity to Type II topoisomerase poisons that trap the cleavable complex intermediates of the target enzymes. The strategy of varying the levels of the target for the desired antibacterial compound, wherein increased target levels translates into increased sensitivity to the antibacterial compound, parallels the approach described above with respect to the Topo I poisons.

Thus, according to the present invention, bacterial screens are provided for identifying Type II poisons, i.e., those compounds that trap the cleavable complex intermediate of the bacterial Type II DNA topoisomerases. According to a preferred embodiment of the invention, bacterial assays are performed comprising contacting a test compound to bacterial test strains that are isogenic except for the fact that one of the strains has a reduced level of bacterial Type II DNA gyrase targets, while the second strain has an increased level of Type II Topo IV targets. According to a preferred embodiment, one strain has a reduced level of the gyrase enzyme while the other strain has an increased level of the Topo IV enzyme. Since this screen is for the detection of Type II topoisomerase poisons, the isogenic strains used can be either topA$^-$ or topA$^+$ as long as they are isogenic for the topA gene. As noted above, the strain with reduced levels of the gyrase enzyme will possess a decreased number of targets for a Type II-specific poison whereas the strain with increased levels of Topo IV will possess an increased level of targets for a Type II-specific poison. The strains are contacted with a test compound and the differential sensitivity of the cells are measured. A test compound that causes an increased DNA damage, growth inhibition and/or killing of the strain with the elevated level of Type II DNA topoisomerase, relative to the strain having reduced levels of Type II targets, indicates that the test compound works in concert with the Type II topoisomerase enzymes to poison the cell and hence is identified as an antibacterial Type II DNA topoisomerase poison.

For example, according to a preferred embodiment of the invention, topA-deleted test strain A contains a compensatory mutation in the gyrA and/or gyrB genes that reduces the level of DNA gyrase in the cell and topA-deleted test strain B contains a compensatory mutation (i.e., a duplication) in the parC and/or parE genes that increases the levels of Topo IV in the cell. See FIG. 2 for an illustration of the genetic events involved in the construction of the isogenic topA-deleted strains of this screen. See also Section 6.1 and Table I, infra, for a description of the construction of specific novel test strains to be used for this screen, e.g., SAD17 or SAD18 (gyrB mutants) versus SAD16 (parC:E duplication mutant). See also Table II, in Section 6.2, infra, for a list of possible isogenic test strain pairs that can be used in the Type II screens of this invention.

The two strains are exposed to a test compound and the differential sensitivity of the cells to the compound is measured. Exposure of the two strains to a test compound that is a Type II topoisomerase poison that traps the cleavable complex intermediate of both the gyrase and Topo IV Type II topoisomerases will result in a significant differential sensitivity between the two strains since strain A contains Type II target levels below wild type while strain B contains Type II target levels above wild type. See FIG. 5 for a schematic depiction of this screen.

As noted supra, in an alternative embodiment of this screen, test strains A and B containing a gyrA and/or gyrB mutation and a parC and/or parE mutation, respectively, can be topA$^+$. Such strains can be constructed as described in Section 6.1, infra, e.g., RFM431 or SAD19 (gyrB mutants) versus SAD15 (parC:E duplication mutant).

Because the screens of this embodiment involve two different Type II topoisomerase targets, additional tests can be performed to determine whether the poison is in fact interacting with both targets (as in the case of the quinolone antibiotics) or either target alone. Further characterization of the Type II poison can involve comparing the differential sensitivities displayed by the test strains with the differential sensitivities displayed by those test strains with respect to known antibiotic and other antibacterial drugs. For example, the quinolone antibiotics are known to be Type II poisons that trap the intermediates of both gyrase and Topo IV; therefore, comparison of the differential sensitivity displayed by the test strains to a test compound according to this invention with the differential sensitivities those same strains display to a known quinolone antibiotic can confirm the discovery of novel compounds with a mechanism of action similar to that of the quinolones. In addition, DNA damage assays and/or DNA cleavage assays for the detection of DNA damage caused by the test compound allows for a further confirmation of the compound as a Type II poison.

In alternative screens for Type II poisons, the sensitivity of strains with reduced gyrase levels or increased Topo IV levels can be separately tested against an isogenic wild type strain. This embodiment of the invention allows for the detection of antibacterial compounds that interact with one or the other of the Type II topoisomerases. Please note that since this screen involves a comparison with a strain that is wild type for the Type II topoisomerases and the test strains must be isogenic and viable, both strains in this embodiment should be topA+.

For example, in this embodiment, bacterial strains A and B are isogenic except that strain A contains a mutation in a gyr gene which results in reduced gyrase levels within the mutant strain while strain B is wild type for the gyr gene. Test compounds are then contacted to the test strains and the differential sensitivity of the strains relative to each other is measured. A test compound that causes a decreased sensitivity on the part of strain A containing a gyr mutation relative to the wild type strain B, is identified as a Type II DNA gyrase poison. Novel strains that can be used in this embodiment include RFM431 or SAD19, which are gyrB mutants, versus wild type RFM430; see Section 6.1, infra, for details of the construction of these strains. Alternatively, bacterial strains A and B can be isogenic except that strain A contains a mutation in a parC and/or parE gene which results in increased Topo IV levels within the mutant strain while strain B is wild type for those genes. Test compounds are then contacted to the test strains and the differential sensitivity of the strains relative to each other is measured. A test compound that causes an increased sensitivity on the part of strain A containing a parC and/or parE mutation relative to the wild type strain B, is identified as a Type II Topo IV poison. Novel strains that can be used in this embodiment include SAD15, which is a parC:E duplication mutant versus wild type RFM430 (see Section 6.1 and Table I, infra).

6. EXAMPLE

The subsections below describe specific embodiments of the compositions and assays of this invention and are provided solely for the purpose of illustration; they are not in any way meant to limit the scope of the present invention.

6.1 Construction/Description of the Bacterial Tests Strains of the Invention Table I below lists various strains that can be used in accordance with the present invention. The table indicates the relevant genotype of each strain as well as the type of mutation possessed by the strain which is relevant to this invention.

TABLE I

| STRAIN | RELEVANT GENOTYPE | RELEVANT MUTATION |
|---|---|---|
| N99 | rpsL galK2 | |
| N4177 | rpsL galK2 gyrB221 gyrB203 | gyrB topA+ |
| GR4413 | sulA::Mudlac | |
| RFM430 | rpsL galK2 ΔtrpE | |
| RFM431 | rpsL galK2 ΔtrpE gyrB221 gyrB203 | gyrB, topA+ |
| SAD15 | rpsL galK2 ΔtrpE (parC,E-duplication::Tn10dkan | TopoIV, topA+ |
| SAD19 | rpsL galK2 ΔtrpE gyrB225 | gyrB, topA+ |
| SAD17 | rpsL galK2 gyrB221 gyrB203 ΔcysBtopA | gyrB, topA− |
| SAD16 | rpsL galK2 parC,E-duplication::Tn10dkan ΔcysBtopA | TopoIV, topA− |
| SAD18 | rpsL galK2 gyrB225 ΔcysBtopA | gyrB, topA |

TABLE I-continued

| STRAIN | RELEVANT GENOTYPE | RELEVANT MUTATION |
|---|---|---|
| SAD20 | rpsL galK2 ΔtrpE /placP-coli topA | |
| SAD21 | rpsL galK2 ΔtrpE /placP-StaphA topA | |
| SAD22 | rpsL galK2 ΔcysBtopA /placP-coli topA | topA− inducible topA |
| SAD23 | rpsL galK2 ΔcysBtopA /placP-StaphA topA | topA− inducible topA |
| SAD24 | sulA::Mudlac /placP-coli topA | |

More specifically, in order to insure isogenic sets of test strains, all bacterial strains used for the identification of topoisomerase poisons were constructed in the genetic background defined by strain N99 (also known as W3102, see Bachmann, in *Escherichia coli* and *Salmonella typhimurium*: Cellular and Molecular Biology, 1st ed., Neidhardt (ed.), p. 1201, ASM Press 1987). The gyrB temperature-sensitive/coumermycin-resistant allele, gyrB221 (cou$^R$) gyrB203(Ts), was isolated in this genetic background as previously described (Menzel and Gellert, 1983, Cell 34: 105–113). To ensure an isogenic derivative, this allele was reintroduced into N99 to produce strain N4177 (genotype: N99 gyrB221 (cou$^R$) gyrB203(Ts)), using phage P1 transduction (Silhavy et al., Experiments with Gene Fusions, Cold Spring Harbor Laboratory, Cold Spring Harbor, N.Y. 1984) by selecting coumermycin resistance (20 μg/ml) and scoring the co-inheritance of the temperature sensitive phenotype.

Next, to facilitate the introduction of a topA defect, a trpE deletion was placed in the N99 and N4177 genetic backgrounds by the sequential phage P1-mediated transduction of pyrB ΔtrpE zci::Tn10 (with phage grown on PLK831) by the selection of tetracycline resistance, followed by the transduction of Ura+ (pyrB+) and the retention of a Trp− (ΔtrpE) tetracycline-sensitive strain to produce strains RFM430' and RFM431', respectively. Strains RFM430 and RFM431 have been previously described; see, e.g., Drolet et al., 1995, Proc. Natl. Acad. Sci. USA 92: 3526–3530. To create a strain with an alternate gyrB allele (gyrB225) capable of compensating for the loss of the topA gene product, the temperature-sensitive character of RFM431' was transduced with phage P1 grown on DM800(genotype: Δ(topA cysB)204 acrA13 gyrB225); see McEachern and Fisher, 1989, FEBS Lett 253: 67–70) to growth at 42° C. and co-inheritance of the wild type coumermycin-sensitive character was scored to produce strain SAD19. The topA gene was deleted from RFM431' and SAD19' by transduction to Trp+ with phage P1 grown on DM800, resulting in the retention of Cys− (ΔcysBtopA) transductants such as SAD17' and SAD18', respectively. These two strains are topA−, gyrB mutants (see Table I above).

Strain SAD17' has the unusual property of being both temperature-sensitive (due to the gyrB$^{TS}$ allele) and cold-sensitive (due to the combination of the ΔcysBtopA mutation and the gyrB$^{TS}$ allele which fails to compensate for the topA deletion at low temperature, e.g., 25° C.). Strain SAD17' was therefore used to select for the transposon-mediated duplication (Anderson and Roth, 1979, Cold Spring Harb. Symp. Quant. Biol. 43. Pt. 2: 1083–1087) of the parc,E genes following transposon mutagenesis at 18° C., using the transposon Tn10dkan (Eliot and Roth, 1988, Mol. Gen. Genet. 213 (2–3): 332–338). The duplicated nature of the compensatory mutation was verified by demonstrating the unstable character of kanamycin resistance and the co-segregation of kanamycin resistance with the ability to grow at 30° C. A Tn10dkan transposon from such an isolate was transduced by phage P1 into strain RFM430' to form strain SAD15'. SAD15' was subsequently transduced to Trp+ with phage P1 grown on DM800, and a Cys− (ΔcysBtopA) transductant, SAD16', was obtained.

In order to improve the sensitivity of the test strains to the test compounds to be screened, derivatives of the strains described above were made hyperpermeable by introduction of the imp4312 mutation. To do so, P1vir was grown (Silhavy et al., supra) on BAS1329 (imp4312 leu::Tn10, Sampson et al., 1989, supra) and used to transduce strains such as SAD15', 16', 17' and RFM431' to tetracycline resistance. Strains co-inheriting the Imp phenotype were identified as described in Sampson et al., supra. The imp-derivatives were the test strains used in the actual screening described below. For the purposes of this disclosure, the imp+ precursors of these strains are designated herein with a prime symbol (e.g., precursor strain SAD'; actual test strain for screening SAD).

In order to obtain test strains containing an inducible topA gene, strain RFM430 is transformed with plasmids, PECOTOP or PSTPTOP to form strains, SAD20 and SAD21, respectively. PECOTOP contains a functional $E.$ $coli$ topA gene operably linked to a tac promoter and can be formed as follows: PCR primers, OGTGAATATGGGTAAAGCTC (SEQ ID NO:1) and GCTCTTCCACCAGTGGC (SEQ ID NO:2) are used to amplify DNA corresponding to the $E.$ $coli$ topA gene from an $E.$ $coli$ genomic library (Clontech, Palo Alto Calif.) using the Advantage-HF PCR kit (Clontech) according to manufacturer's recommendations. These PCR fragments are then cloned into the pGEM-T vector and transformed into the host strain JM109 (Promega, Madison Wis.). Fidelity of the product can be verified by DNA sequence analysis according to standard procedures and would be expected to be identical with the published sequence (see, e.g., European patent application EP 0 835 938 A2). To create a regulated expression clone, these sequences are excised from the PGEM clone and used to replace the human Topo I gene that is contained in the plasmid pMStop1 which is described in Taylor and Menzel, 1995, Gene 167: 69–74. Techniques for incorporating the $E.$ $coli$ Topo I sequences from the PGEM clone into PMSTOP1 are standard and commonly practiced by those of ordinary skill in the art (see, e.g., Ausubel et al., 1989–1997, Current Protocols in Molecular Biology, supra). The resultant product is PECOTOP (FIG. 3A), which is transformed into strain RFM430 to create strain SAD20. Strain SAD22 can then be derived from SAD20 by transduction to Trp+ and retention of the cys− (Δcystop) co-transductant using bacteriophage P1 as described above for the creation of SAD17 from RFM431.

Similarly, PSTPTOP, which contains a functional $S.$ $aureus$ topA gene operably linked to a tac promoter, can be constructed as described above using PCT primers, TGGGCAGCAGCCATCATCA (SEQ ID NO:3) and TTATTTCTGCGCTGCCTCTT (SEQ ID NO:4) for the amplification of DNA corresponding to the gene for $S.$ $aureus$ Topo I from an $S.$ $aureus$ genomic library (Clontech). As above, the PCR fragments can be cloned into the PGEM-T vector and transformed into JM109 and subsequently excised therefrom o replace the human Topo I gene of PMSTOP1. The resultant PSTPTOP plasmid (FIG. 3B) is transformed into strain RFM430 to create strain SAD21.

Strain SAD23 is then constructed from SAD21 by transduction to Trp+ and retention of the cys− (Δcystop) co-transductant using bacteriophage P1 as described above. Strain SAD24 is formed by the transformation of strain GR4413 with PECOTOP.

6.2 Differential Sensitivity Assay in Agar

The following procedure was used for the identification of bacterial Topo I poisons as well as bacterial Type II topoisomerase poisons. Generally, paired test strains were grown in culture and then transferred to agar plates. If bacterial strains with the imp mutation are used, i.e., to increase permeability to the test compound, the strains should not be kept on agar (either on a plate or on a slant) for more than a day or two. The cultures which were the source of the cells used for screening can be stored either at −80° C. or preferably, in 20% glycerol at −20° C. Such a working frozen glycerol stock can be used for up to a year. Small aliquots of the frozen culture were used to inoculate liquid broth prior to each experiment.

As examples of the screens of this invention, a Topo I screen compared strains SAD15 and SAD16, whereas a Type II topoisomerase screen compared SAD16 and SAD17 (see, e.g., Section 6.1 and Table I, supra and Table II, infra). As indicated in Table II, infra, screens similar to those exemplified herein can be readily performed using the paired test strains listed in that Table.

In preparation for the screen, between 50–100 $\mu$l of frozen solid from each "working frozen", i.e., for each one of the paired test strains to be tested, was used to inoculate a 5 ml culture of liquid Luria Broth (LB) containing appropriate antibiotics, and the cultures were grown aerobically overnight at 37° C. with gyratory shaking. Strains containing the parC,E duplication such as SAD 15 and SAD16 were grown in the presence of 25 mg/ml kanamycin and 12.5 mg/ml tetracycline, whereas strains containing the gyrase mutation such as SAD17 were cultured in 12.5 mg/ml tetracycline. These overnight cultures were then subcultured 1:40 in LB media without antibiotics 4 to 5 hours prior to final plate preparation and the cell OD at $A_{600}$ was measured.

Prior to the assay procedure, plates (bottom agar) were prepared by adding 30 ml of LB media with 1.5% agar in 125×84 mm rectangular petri dishes. The plates were allowed to solidify and stored inverted at least 24 hours prior to use to permit drying. For the assay, fresh cells from each test strain prepared as described above were added to liquified top agar (LB+1.0% low melt agarose at 37° C.) such that 0.08 $A_{600}$ OD units of cells were added per ml. The liquid top agar mixture (12 ml per plate) was poured onto the bottom agar and allowed to harden for at least one hour at room temperature prior to application of the test compound.

Test compounds (dissolved in 100% DMSO at a nominal concentration of 2.5 Mm) arrayed in microtiter plates were delivered (1 $\mu$l) to the agar surface using a 96-pin device (VP Scientific, San Diego Calif.). In the Type II screens, dilutions of the DNA gyrase poison, Norfloxicin, were included in control wells. Plates were inverted and incubated overnight at 37° C.

After 24 hours of incubation, the plates were removed and scored for the presence of clearing zones—areas where bacterial growth is not apparent against a background lawn of growth. A differential growth inhibition, i.e., a zone of no or reduced growth exhibited by one of the strains of the pair compared to the other (where identical samples of a test compound have been applied) indicates that test compound is a Topo I or Type II topoisomerase poison, depending upon the particular screen performed.

For example, FIG. 4A depicts a typical Topo I screen of the invention, wherein an otherwise isogenic test strain pair, i.e., strains that are isogenic except that one strain is topA⁻ and the other is topA⁺, are exposed to a test compound. A test compound that acts as a general poison will create a zone of growth inhibition on both the topA⁻ and topA⁺ plates. A test compound that is non-poisonous will create no zone of inhibition on either plate. However, a test compound that is a Topo I poison, i.e., acting through its effect on Topo I targets, can only inhibit the topA⁺ test strain which will show a zone of inhibition; since the topA-deleted test strain does not contain a Topo I target, it will demonstrate no zone (or a dramatically reduced zone) of inhibition.

In fact, in the specific Topo I poison screen exemplified herein, wild type, topA⁺ test strain SAD15 and its isogenic, topA⁻ companion strain SAD16 were tested with various test compounds and in numerous instances, a zone differential of growth inhibition was observed, i.e., SAD15 exhibited a zone of inhibition whereas SAD16 did not, or exhibited a very small zone of inhibition. Those test compounds that gave these results were considered Topo I poisons and were arrayed to new plates and retested to confirm activity (see Results Section 6.3, infra). As indicated in FIG. 4A and in Table II below, similar screens can be run with paired, isogenic strains RFM431/SAD17 and SAD19/SAD18.

In the embodiment of the Topo I screen of the invention wherein the test strain contains an inducible promoter for the expression of the topA gene, the test strain containing the inducible gene is treated so as to induce the production of Topo I prior to exposure to the test compound. For example, in this embodiment, 10 cm petri dishes containing 40 ml of LB-agar with 50 μg ampicillin/ml with (+) or without (−) IPTG are overlaid with $10^8$ midlog topA-deleted test strain cells in 4 ml of soft (0.7% agar) LB-agar at 48° C. When the soft-agar overlays have solidified, 4 mm cylindrical holes or wells are cored to the bottom of each petri dish using a small probe attached to a vacuum. The test compound is then added to the wells and the zones of inhibition around the wells are measured after 14–18 h of growth at 30° C.

For example, as depicted in FIG. 4B, either of the topA-deleted test strains SAD22 and SAD23, which contain, respectively, the PECOTOP and PSTPTOP plasmids described in Section 6.1 above and depicted in FIGS. 3A and 3B, can be grown with or without IPTG (an inducer of topA expression through its effect on the laci gene of the plasmid). When the inducer is present, the topA gene will be expressed and produce Topo I targets in the form of the Topo I enzyme; without the presence of the inducer, the strain will lack or have reduced Topo I targets.

Application of a test compound to the plates containing the test strain in an induced vs. non-induced or low-induced condition, will indicate whether that test compound is a Topo I poison as follows: A general poison will produce an essentially identical zone of inhibition on both plates, while a compound that is not a poison will demonstrate no zone of inhibition on either plate. However, a Topo I poison Go 15 will produce a larger zone of growth inhibition on the induced plate than on the non- or low level-induced plate since the induced test strain will contain a greater number of Topo I targets for interaction with the poison than the non- or low-induced strain.

Similarly, test strains SAD20 and 21, which contain the PECOTOP and PSTPTOP plasmids, respectively, can be used in this inducible Topo I screen wherein either strain can be grown in the presence of IPTG for high level expression of Topo I and compared with the strain in an uninduced condition, i.e., having a wild type level of Topo I expression. A differential zone of growth inhibition displayed by the test pair upon exposure to a test compound indicates that the test compound is a Topo I poison.

Figure 5:
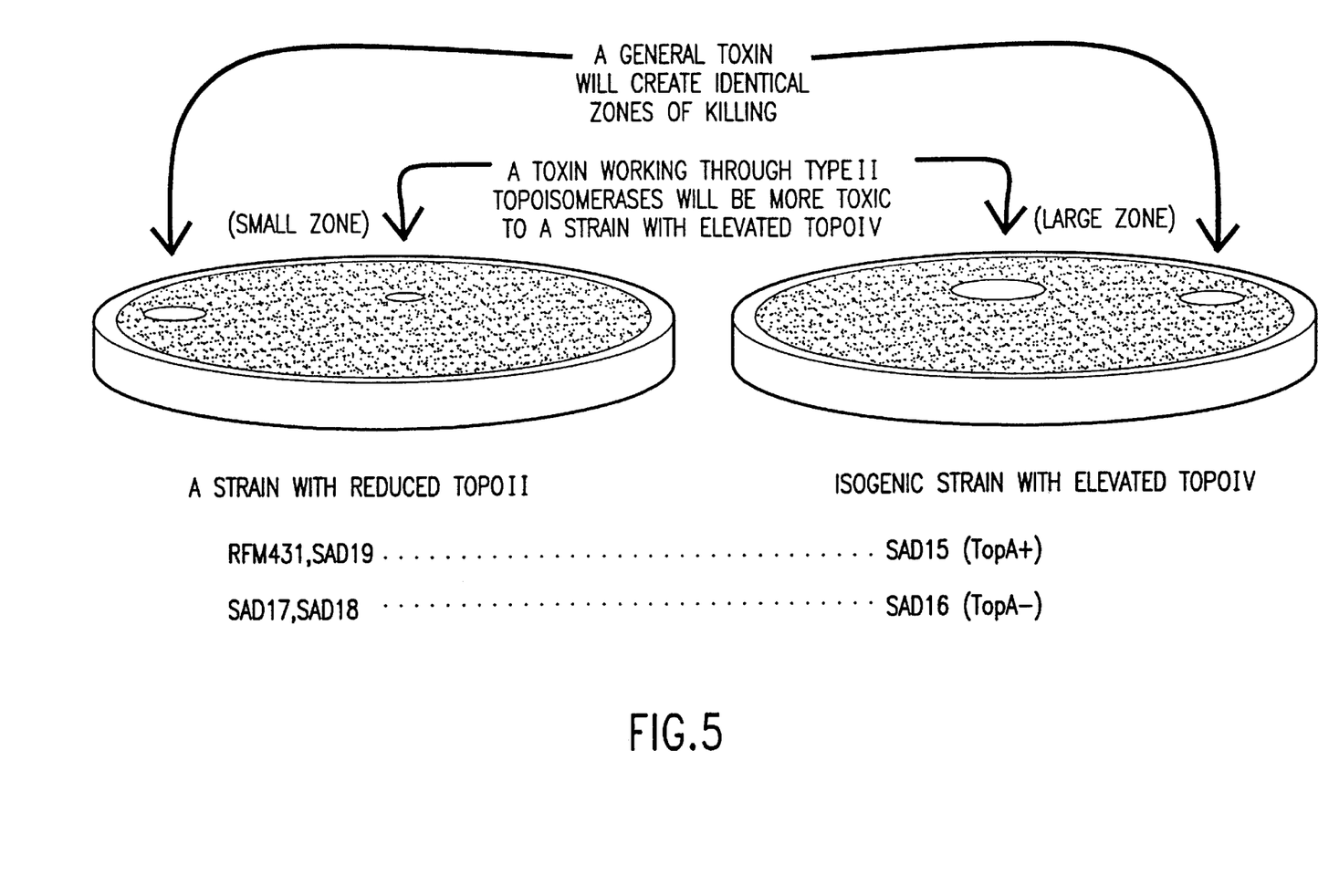
FIG. 5. Schematic depiction of a Type II topoisomerase poison screen comparing strain A containing reduced levels of DNA gyrase with strain B containing elevated levels of Topo IV.

As to the Type II topoisomerase poison screen of the invention, the procedure was the same as described above utilizing the appropriate isogenic test strains, e.g., one strain that contained a reduced level of Type II topoisomerase targets and the other strain that contained an elevated level of such targets. According to a preferred embodiment, isogenic strains, one of which contains a mutation in the gyrA and/or gyrB genes and one of which contains a duplication of the parC and/or parE genes, were utilized. As indicated in FIG. 5, according to this screen, a test compound that is a Type II topoisomerase poison will create a larger zone of growth inhibition on the plate containing the strain having the greater level of Type II targets for the poison. As noted above, strains SAD16 and SAD17 were tested using this screen. Numerous test compounds gave a differential zone of growth inhibition in this screen, i.e., SAD16 exhibited a greater zone of inhibition than SAD17. See, e.g., Section 6.3, infra for results. As indicated in FIG. 5, other isogenic test strain pairs that can be used in this Type II screen include RFM431 and SAD15, SAD19 and SAD15, and SAD18 and SAD16. In addition, test strain pairs RFM431/RFM430, SAD19/RFM430 or SAD15/RFM430 could also be used.

Table II below sets forth various pairs of isogenic strains that can be used in the Topo I or Type II poison screens of this invention.

TABLE II

Pairs of Isogenic Strains
For Use In The Screens of The Invention

| TOPO I POISON SCREENS | TYPE II POISON SCREENS |
|---|---|
| SAD15/SAD16 | RFM431/SAD15 |
| RFM431/SAD17 | SAD19/SAD15 |
| SAD19/SAD18 | SAD17/SAD16 |
| SAD22 INDUCED/NON-INDUCED | SAD18/SAD16 |
| SAD23 INDUCED/NON-INDUCED | RFM431/RFM430 |
| SAD20 INDUCED/NON-INDUCED | SAD19/RFM430 |
| SAD21 INDUCED/NON-INDUCED | SAD15/RFM430 |

6.3. Test Compound Results of Screens

Using the Topo I screen exemplified above, 19 test compounds were scored as Topo I poisons and six have been confirmed as such to date, using the DNA damage assay and the DNA cleavage assay described in Sections 6.4 and 6.5, infra, respectively. These poisons have also been shown to inhibit relaxation by bacterial Topo I in an inhibition assay described by Tse-Dinh, Y- C. et al., 1988, J. Biol. Chem. 263: 5560–5565 and to have cleaved DNA in the presence of bacterial Topo I enzyme using techniques as described in Tse-Dinh, Y- C., 1986, J. Biol. Chem. 261: 10931–10935 and Zhu et al., 1998, J. Biol. Chem. 273: 8783–8789.

Using the Type II poison screen exemplified above, 56 test compounds were scored as Type II poisons and of these, seven have been confirmed to date, using the DNA damage and DNA cleavage assays described infra. These compounds have also been shown to inhibit DNA gyrase using techniques as described by Reece and Maxwell, 1989, J. Biol. Chem. 266: 3540–3546. Two of these poisons are quinolones, an expected compound class as discussed supra, thus confirming the screening procedure. Five of the seven confirmed poisons represent novel structures not previously reported to have Type II inhibitory activity.

In addition, because quinolones were known to be Type II poisons, known quinolones were run as controls in the Type II screen of the invention to verify its validity. Furthermore, Table III below shows the results of a Type II poison screen of the invention using two quinolone compounds, which are known to be Type II topoisomerase poisons.

TABLE III

| Compound | Zone Size | |
|---|---|---|
| | SAD16 (elevated type II Topo) | SAD17 (reduced type II Topo) |
| Norfloxicin (50 μg/ml) | 10 mm | 7.0 mm |
| Ciprofloxicin (10 μg/ml) | 11.5 mm | 8.0 mm |
| Ampicillin (1.25 mg/ml) | 8.0 mm | 9.5 mm |
| Echinoinycin (0.25 mg/ml) | 8.0 mm | 8.0 mm |

This table indicates the behavior of the type II topoisomerase test strains SAD16 and SAD17 with two known type II poisons (norfloxicin and ciprofloxicin) and two control antibacterial compounds. The assay was performed as described in Section 6.2, supra. The zone size is the measured diameter of the area around the well where bacterial growth was inhibited. As can be seen, the two quinolones created a larger zone of growth inhibition on SAD16 than on SAD17, a result indicative of a Type II poison (whereas the expected differential sensitivity was not observed with the control antibacterial compounds). This control experiment indicates that the Type II screen of the invention operates as disclosed herein.

6.4 DNA Damage Assay

As noted herein, it may be desirable to confirm the DNA-damaging effect of the Topo I or Type II poisons identified by the screens of this invention. An example of one such confirmatory test is a DNA damage assay wherein the ability of a test compound to cause DNA damage can be assessed by measuring β-galactosidase activity in a culture of E.coli cells containing a DIN (DNA damage inducible) promoter fused to β-galactosidase (Huisman, O. et al., supra; and Kenyon C. et al., 1982, J. Mol. Biol. 160: 445–457) following the exposure of such a culture to the compound in question. For example, in a liquid culture format, strain GR4413 (Huisman et al., supra), which contains the sulA-lac regulatory sequence, was used an inoculum (1:100 from a culture with an A650 value=0.6 OD units) for fresh Luria broth liquid. 190 μl aliquots were added to duplicate 10 μl samples of test compound (in 100% DMSO) distributed into the wells of a flat bottom polystyrene microtiter plate. The microtiter plate was incubated overnight (12–16 hours) at 30° C. without shaking. These cultures in microtiter format were then assayed for β-galactosidase activity as described by Menzel, R., 1989, Anal. Biochem. 181: 40–50. Following this growth and test compound exposure, final cell A650 values were determined using a microtiter reader. These cells were then made permeable by transferring separate 150 μl cultures from each well of the incubation plate to 30 μl of $CHCl_3$ present in the corresponding well of a polypropylene microtiter plate using an automated pipetting device. The cultures were made permeable by repeated pipetting up and down (in place; 10x). At this time, a β-galactosidase assay was initiated by using an automated pipetting device to carefully (so as to not disturb the $CHCl_3$ in the bottom of the microtiter plate well) transfer 20 μl of the $CHCl_3$-treated culture to 180 μl of prewarmed (28° C.) Z-buffer (60 mM $Na_2HPO_4$, 40 mM $NaH_2PO_4$, 10 mM KCl, 1 mM $MgSO_4$, and 50 mM β-mercaptoethanol) with 1 mg/ml chlorophenol-red β-D-galactopyranoside (CPRG) present in each of the wells of a clear flat bottom polystyrene microtiter plate. The assay's progress was monitored by immediately transferring the plate to a microtiter reader (with a 28° C. temperature controlled chamber) and following the change in A595 (Eustice, D. C. et al., 1991, BioTechniques 11: 739–742). Final β-galactosidase specific activities (normalized to a cell A650 of 1.0 to adjust for differences in growth) were calculated from a kinetic assay as described by Menzel, 1989, supra. Compounds causing significant increases in β-galactosidase activity (>2x) were judged to be active in this DNA damage assay.

Alternatively, the ability of compounds to cause DNA damage was assessed in an agar plate format. To perform this assay, 400 ml of Luria broth with 1.5% agar was sterilized and allowed it to cool to 50° C., followed by the addition of 10 ml of an inoculum culture (GR4413 A650 value=0.6 OD units) and 3.2 ml of a 50 mg/ml 5-bromo-4-chloro-3-phenol-indolyl-β-D-galactopyranoside(X-gal) in dimethylformamide. 40 ml aliquots of this mixture were poured into 125×84 mm rectangular petri dishes and the agar was allowed to solidify. Compounds to be tested were applied to the surface of the agar in aliquots of 1–2 μl using commercially available 96 prong applicator devices (VP Scientific; San Diego, CA). For larger volumes (3–20 μl), wells may be cored into the agar and then filled with the test compound. In all cases, responses must be compared to solvent controls. Any material showing a response (a zone of hydrolyzed blue X-gal) stronger than the solvent control alone was considered positive, i.e., a DNA damage signal.

6.5 DNA Cleavage Assay

To perform the cleavage assay, a plasmid substrate, such as pBR322, was cut with a restriction endonuclease (e.g., EcoR1) to convert the substrate into a linear form. This linear substrate was radioactively end-labeled employing standard methods well known to those practiced in the art (see Ausubel, supra or Chen et al., 1984, Proc. Natl. Acad. Sci. 259: 13560–13566). The actual cleavage reaction (20 μl) was performed by mixing the test compound, the end-labeled DNA fragment (50 ng) and the appropriate purified topoisomerase enzyme, e.g., either E. coli DNA gyrase (Reece and Maxwell, supra), topoisomerase IV (Peng and Marians, 1993, J. Biol. Chem. 268: 24481–24481), E. coli topoisomerase I (Tse-Dinh, Y- C. et al., 1988, J. Biol. Chem. 263: 5560–5565) or human topoisomerase II (as a control) (Chen et al., supra) in their appropriate respective buffers at 37° C. The cleavage reaction was terminated after 30 minutes through denaturing the topoiosomerases by making reaction buffer 0.5% SDS. Subsequent to this protein denaturation step, DNA was freed from the topoisomerase-DNA cleavage product by protease treatment (1 μl of 1.5 mg/ml proteinase K per 20 μl, 1 hour at 42° C.). The samples were then deproteinized with $CHCl_3$-phenol as described by Ausubel, supra, and electrophoresis was used to resolved the end-labeled cleavage products on either agarose gels (1%, low resolution) or acrylamide gels (8%, 29:1 acrylamide to bis, for high resolution) according to standard procedures. Following electrophoretic resolution, visualization of the products was accomplished by autoradiography. Cleavage was indicated by the appearance of discrete low molecular weight species.

What is claimed:

1. A method for screening for antibacterial compounds that interact with bacterial DNA Topoisomerase I comprising:
   (a) providing at least one pair of bacterial test strains that are isogenic except that one of the strains contains a topA mutation that results in a reduced level of DNA Topoisomerase I targets within said test strain relative to the other strain, wherein the isogenic test strain pair is selected from the group consisting of SAD15 and SAD16, RFM431 and SAD17, and SAD19 and SAD18;
   (b) contacting a test compound to the test strains; and
   (c) detecting a differential sensitivity between the test strains to the test compound.

2. The method of claim 1 wherein the differential sensitivity of the strains is detected by measuring DNA damage to the bacterial strains after exposure to the test compound.

3. The method of claim 2 wherein DNA damage is measured by assays which measure cell death or assays which measure growth inhibition.

4. The method of claim 2 wherein the DNA damage is measured by DNA damage assays or DNA cleavage assays.

5. A method for screening for antibacterial compounds that interact with bacterial DNA Topoisomerase I comprising:
   (a) providing at least two separate cultures of a bacterial test strain that contains a topA mutation that results in a reduced level of DNA Topoisomerase I targets within the test strain, which strain additionally contains a functional topA gene operably linked to an inducible promoter, wherein the bacterial test strain is selected from the group consisting of SAD22 and SAD23;
   (b) growing the first culture of the strain under conditions in which the strain is induced to produce DNA Topoisomerase I;
   (c) separately growing the second culture of the strain under conditions of either no induction or a low-level induction compared to the induction of step (b);
   (d) contacting a test compound to the cultures grown according to (b) and (c); and (e) detecting a differential sensitivity to the test compound between the cultures grown under the different conditions.

6. The method of claim 5 wherein the inducible promoter is selected from the group consisting of the tac promoter, the lac promoter, ara-based promoters and tet-based promoters.

7. The method of claim 5 wherein the differential sensitivity is detected by measuring DNA damage to the bacterial strains after exposure to the test compound.

8. The method of claim 7 wherein DNA damage is measured by assays which measure cell death or assays which measure growth inhibition.

9. The method of claim 7 wherein the DNA damage is measured by DNA damage assays or DNA cleavage assays.

10. A method for screening for antibacterial compounds that interact with bacterial Type II DNA topoisomerases comprising:
    (a) providing at least one pair of bacterial test strains that are isogenic except that one of the strains has a reduced level of bacterial Type II DNA gyrase targets and the other strain has an increased level of Type II Topoisomerase IV targets, wherein the isogenic test strain pair is selected from the group consisting of RFM431 and SAD19 and SAD15, SAD17 and SAD16, and SAD18 and SAD16;
    (b) contacting a test compound to the test strains;
    (c) detecting a differential sensitivity between the test strains to the test compound; and
    (d) identifying the test compound as an antibacterial compound.

11. The method of claim 10 further comprising comparing the differential sensitivity displayed by the test strain pair to the test compound with the differential sensitivity displayed by the same test strain pair to other known antibacterial compounds.

12. A method for screening for antibacterial compounds that interact with bacterial DNA Topoisomerase I comprising:
    (a) providing at least two separate cultures of a bacterial test strain that contains a topA mutation that results in a reduced level of DNA Topoisomerase I targets within the test strain, which strain additionally contains a functional topA gene operably linked to an inducible promoter on a plasmid selected from the group consisting of PECOTOP and PSTPTOP;
    (b) growing the first culture of the strain under conditions in which the strain is induced to produce DNA Topoisomerase I;
    (c) separately growing the second culture of the strain under conditions of either no induction or a low-level induction compared to the induction of step (b);
    (d) contacting a test compound to the cultures grown according to (b) and (c); and
    (e) detecting a differential sensitivity to the test compound between the cultures grown under the different conditions.

13. A method for screening for antibacterial compounds that interact with bacterial DNA Topoisomerase I comprising:
    (a) providing at least two separate cultures of a bacterial test strain that is wild-type for the topA gene and additionally contains a functional topA gene operably linked to an inducible promoter, wherein the bacterial test strain is selected from the group consisting of SAD20 and SAD21;
    (b) growing the first culture of the strain under conditions in which the strain is induced to produce increased levels of DNA Topoisomerase I;
    (c) separately growing the second culture of the strain under conditions of either no induction or a low-level induction compared to the induction of step (b);
    (d) contacting a test compound to the cultures grown according to (b) and (c); and
    (e) detecting a differential sensitivity to the test compound between the cultures grown under the different conditions.

* * * * *